United States Patent [19]

Kishimoto et al.

[11] Patent Number: 5,248,806
[45] Date of Patent: Sep. 28, 1993

[54] METHOD OF PREPARING α-L-ASPARTYL-L-PHENYLALANINE METHYL ESTER

[75] Inventors: Shinichi Kishimoto; So Abe; Toshihisa Kato, all of Kawasaki, Japan

[73] Assignee: Ajinomoto Co., Inc., Tokyo, Japan

[21] Appl. No.: 885,977

[22] Filed: May 20, 1992

[30] Foreign Application Priority Data

May 23, 1991 [JP] Japan .................................. 3-221335

[51] Int. Cl.⁵ ............................................ C07C 103/52
[52] U.S. Cl. ....................................................... 560/41
[58] Field of Search ........................................... 560/41

[56] References Cited

U.S. PATENT DOCUMENTS

| 4,606,854 | 8/1986 | Ozawa et al. | 560/19 |
| 4,618,695 | 10/1986 | Ozawa et al. | 560/41 |

FOREIGN PATENT DOCUMENTS

| 0128694 | 12/1984 | European Pat. Off. |
| 0405273 | 1/1991 | European Pat. Off. |
| 145298 | 6/1988 | Japan |

*Primary Examiner*—José G. Dees
*Assistant Examiner*—Samuel Barts
*Attorney, Agent, or Firm*—Oblon, Spivak, McClelland, Maier & Neustadt

[57] ABSTRACT

An acid addition salt of α-APM is dissolved or suspended in an aqueous medium at 50° C. or lower at a pH of 3 or less and a concentration of the salt of 3 wt.% or more (solution A). A liquid having a pH of 3 or more and containing or not containing α-APM is prepared (solution B) and gradually mixed with solution A with stirring. The temperature of the liquid mixture is kept to be 40° C. or lower and the pH value of the mixture is kept at 3 or more, optionally adding a base thereto, whereby crystals of α-APM are precipitated out.

7 Claims, No Drawings

METHOD OF PREPARING α-L-ASPARTYL-L-PHENYLALANINE METHYL ESTER

BACKGROUND OF THE INVENTION

1. Field of the Invention

The present invention relates to a method of preparing α-L-aspartyl-L-phenylalanine methyl ester (α-APM) which is useful as a sweetener and more specifically to an improved method of preparing α-APM by neutralizing an acid addition salt of α-APM with a base.

2. Discussion of the Background

α-APM of the present invention is a dipeptide sweetener having a sweetness of about 200 times that of sucrose (cane sugar). Because of its good quality sweetness and low calorie content, it has become widely used as a diet sweetener, and the worldwide demand for it is estimated to be over 10,000 tons by 1995.

α-APM is produced industrially by several methods. In one method, an N-substituted aspartic acid anhydride and a phenylalanine methyl ester are reacted and bonded together in an organic solvent and the N-substituent is then removed from the product (U.S. Pat. No. 3,786,039). A second method of obtaining α-APM is to methyl-esterify α-L-aspartyl-L-phenylalanine in a mixed solvent comprising water, methanol and hydrochloric acid to obtain α-APM hydrochloride, and then neutralize the salt to obtain α-APM (Japanese Patent Application Laid-Open No. 53-82752). A third method of obtaining α-APM is to condense an N-substituted aspartic acid and a phenylalanine methyl ester in the presence of an enzyme and then remove the N-substituent from the product (Japanese Patent Application Laid-Open No. 55-135595).

In the first chemical synthetic method noted above, the β-isomer (β-L-aspartyl-L-phenylalanine methyl ester) is produced as a side product. As a means of selectively removing impurities including the β-isomer, a purification method is used in which α-APM containing impurities is brought into contact with a hydrohalogenic acid and then subjected to solid-liquid separation to isolate α-APM as its hydrohalide salt.

Where industrial scale production of α-APM is required to meet the current demands, chemical methods are the major methods from the viewpoint of reducing the manufacturing cost. In this case, esterification is often effected via its hydrochloride salt as in the second method noted above, or after formation of α-APM, the hydrohalide salt is formed and purified as described above. To obtain α-APM from its hydrohalide salt, such as its hydrochloride salt, using an ordinary method, the hydrohalide salt of α-APM is dissolved or suspended in an aqueous medium and the resulting solution or suspension is neutralized by adding an aqueous solution of a base such as sodium hydroxide, sodium hydrogen carbonate or ammonia.

However, the present inventors have discovered that when a large amount, above a liter scale, of liquid must be dealt with during an industrial scale neutralization operation, such as the neutralization of an acid addition salt of α-APM, the conventional neutralization method has serious problems.

Specifically, when a base is continuously added dropwise to an aqueous solution of an acid addition salt of α-APM to reach the isoelectric point of α-APM, rapid precipitation of α-APM occurs during the course of the addition so that stirring of the system becomes impossible. In the worst case, it has been found that the stirrer completely stops. If the amount of liquid is at most 100 ml or so, as in a laboratory scale experiment, the precipitated solid phase can be easily broken with a tool, such as a spatula, whereby the fluid condition can be recovered. However, when the amount of liquid is large, i.e., about a liter or more, for example, in a bench plant or the like, or where the neutralization is carried out in a large-scale pilot plant or commercial plant, this method can not be used for solving the problem.

As a countermeasure to this problem in an industrial scale neutralization, addition of a large amount of water may be considered so as to carry out the neutralization using a diluted concentration. However, this lowers the capacity and efficiency of the device used and also lowers the yield of the product. Therefore, dilution is not a good countermeasure.

On the other hand, very slow addition of an aqueous base solution over an extremely long period of time would be effective for ensuring the fluidity of the liquid, but is ineffective from the view point of the production. Still another method is intermittently discontinuing the dropwise addition of the neutralizing agent into the reaction system having a pH range at which precipitation of α-APM starts or a pH value of 2.5 or so, to ripen the precipitated crystals (Japanese Patent Application Laid-Open No. 63-145298). This method has the serious drawback that the pH range suitable for the ripening fluctuates greatly unless the initial concentration of α-APM (or its acid addition salt) is strictly controlled to certain values. The α-APM content in the separated wet crystals (acid addition salt) always fluctuates, depending upon the delicate conditions occurring during the crystallization of the acid addition salt of α-APM. It is difficult, therefore, to keep the initial concentration of α-APM (or its acid addition salt) constant in a dissolution system employing the large amounts of liquid often used in industrial production.

In order to avoid this problem, a complicated concentration control system is necessary to effect batch-wise analysis every time and then to supply crystals or water when needed. Alternatively an expert monitor skilled in the art must be exclusively dedicated to the system to be able to batchwise determine the suitable ripening pH value each time.

Finally, even though these operational problems can be avoided by any of the above-mentioned systems, the α-APM crystals obtained still have extremely poor solid-liquid separability, which requires increased equipment costs and increased energy consumption in the filtration and drying steps used as the post-treatment steps.

A need continues to exist for a method of overcoming the above-mentioned problems in neutralizing an acid addition salt of α-APM.

SUMMARY OF THE INVENTION

Accordingly, one object of the present invention is to provide a method for overcoming the problems associated with neutralizing an acid addition salt of α-APM.

This and other objects which will become apparent from the following specification have been achieved by the present process.

In the present process, an acid addition salt of α-APM is first dissolved or suspended in an aqueous medium to have a concentration of 3 wt.% or more (solution A), and is maintained as an acidic solution having pH of 3 or less. A separate aqueous medium containing or not containing α-APM is prepared as aqueous medium B. Solution A is gradually added to medium B with stirring, while the pH of the resulting liquid mixture is kept a pH 3 or more so that α-APM is crystallized out. A base may be optionally added to medium B. By this process, the above-mentioned problems in operation and filtration are overcome and the yield of the crystallized product is higher than that obtained by the conventional methods.

DETAILED DESCRIPTION OF THE PREFERRED EMBODIMENTS

The process of the present invention drastically reduces the necessary equipment and energy costs and reduces the number of personnel necessary for carrying out the neutralization and crystallization process.

Acid addition salts of α-APM which are suitable for use in the present invention include mineral acid salts such as hydrochloride, hydrobromide, sulfate and phosphate salts. The hydrochloride salt is preferred.

In the present invention, an acid addition salt of α-APM is neutralized in the form of an aqueous solution or suspension. All of the acid addition salt crystals need not be dissolved. As the solvent, water is suitable or a mixed solvent comprising a water-miscible organic solvent and water. Preferred water-miscible organic solvents include $C_{1-4}$alkyl alcohols, in particular methanol and ethanol. The amount of the solvent to be used is determined so that the concentration of the acid addition salt of α-APM in the resulting solution or suspension is 3 wt.% or more.

If the concentration is lower than 3 wt.%, the yield and the production per device capacity are lowered and the filterability of the crystals precipitated out after neutralization rapidly worsens. The upper limit of the concentration is not specifically defined, and may be selected accordingly to the apparatus used, i.e., pipeline, pumps or the like, or for ease of operation of the process. As a general range, the concentration is suitably from about 3 to 25 wt.%.

Blending and neutralization must be effected gradually, in carrying out the method of the present invention, to ensure the solution or suspension of the acid addition salt of α-APM is kept as a solution or suspension during the process. α-APM dissolved in an aqueous medium under low pH conditions is easily hydrolyzed to give α-L-aspartyl-L-phenylalanine (α-AP). This decomposition reaction lowers the yield and quality of the product and is therefore undesireable in production of the product. As the decomposition occurs especially at high temperatures, the temperature of the reaction system must be 50° C. or lower, more preferably 40° C. or lower.

In the case of using wet α-APM acid addition salt crystals, as separated from a previous acid addition salt crystallizing step, the solution or suspension containing the acid addition salt will have a low pH value due to the excess acid in the mother solution which adheres to the wet crystals. This low pH will accelerate decomposition. In order to prevent the accelerated decomposition, partial neutralization of the wet crystals and storage of the thus partially neutralized crystals is desired. In this case, a suitable pH range is from 2 to 3, preferably from 2.3 to 2.8. Slight precipitation of α-APM under these conditions will not interfere with the subsequent neutralization operation or cause problems in carrying out the present invention. However, if the pH value is greater than 3, rapid precipitation of α-APM crystals occurs. Therefore, the partial neutralization should be effected at a pH value of 3 or less.

Suitable base neutralizing agents include alkali hydroxides such as sodium hydroxide, alkali carbonates or bicarbonates such as sodium carbonate and bicarbonate, ammonia and other organic amines, preferably $C_{1-10}$-monoalkyl and dialkyl amines. From the viewpoint of prevention of decomposition of α-APM during neutralization as well as of the cost and the easy operation, sodium carbonate or ammonium, in the form of its aqueous ammonium hydroxide solution, are used.

The other liquid (medium B) to be used for mixing is one which optionally contains α-APM dissolved or suspended therein prior to mixing. Medium B containing α-APM can be prepared, for example, where all of the suspension of α-APM crystals obtained by the method of the present invention are not subjected to solid-liquid separation, but a portion of the crystals are used in the next mixing and neutralization batch; or alternatively only the mother solution obtained by the solid-liquid separation is reused in the next batch. In order to moderate rapid precipitation of α-APM crystals by neutralization, the presence of α-APM crystals in solution B as seed crystals is preferred.

The total amount of liquid must be determined in such a way that the liquid mixture obtained after combining solutions A and B and the neutralizing agent will have a final α-APM concentration of not lower than 3 wt.% after mixing and neutralization, for the purpose of improving the solid-liquid separability and increasing the yield, especially when medium B does not contain α-APM. Medium B may contain the basic compound used for neutralization as noted above. α-APM dissolved in an aqueous medium easily forms a diketopiperazine compound (DKP) under conditions of high pH due to an intramolecular cyclization reaction. Even when medium B contains no α-APM before mixing, it is preferable that a suitable amount of a base, i.e. an amount proportional to the amount of the acid in the acidic solution, is gradually added to solution A in consideration of the local concentration conditions occuring immediately after the initiation of mixing. Preferably, the base is simultaneously added while solution A is added to and mixed with medium B.

Blending is effected with stirring so that local variations of pH, temperature and concentration in the reaction system are minimized. The term "stirring" as referred to herein means causing a forced flow by stirring blades, pump circulation or introduction of air bubbles, and requires a force sufficient to at least float and suspend the crystals existing in the system in the liquid, to form a slurry during the course of the mixing and neutralization steps.

The pH value of the reaction liquid mixture must always be maintained at a pH of 3 or more. The upper limit is desirably 6 from the viewpoint of prevention of decomposition as described above. The final pH value is preferably from 4 to 6.

The liquid temperature should be 40° C. or lower from the viewpoint of prevention of decomposition at high temperatures and of improvement of the yield. The lower temperature limit need not be determined specifically, provided that it is such that the solvent is not frozen. In general, the lower limit will fall within the range of from 5° C. to 30° C. Cooling can be conducted during and/or after adding and mixing solutions A and B to obtain a liquid temperature of 30° C. or less.

The rate of addition of the solution or suspension A of the α-APM acid addition salt to medium B varies, in accordance with the scale (liquid amount) of the process to be carried out. It may have any desired value which does not cause rapid neutralization or precipitation of α-APM crystals, which can result in operational problems.

The mixing and neutralization may be effected in one container in the method of the present invention, but if desired, stepwise mixing and neutralization and, optionally, cooling may be effected with a plurality of reaction containers or vessels connected to each other in series. Where the latter system of several containers is used, the precipitation load of α-APM is dispersed in the plurality of containers which is an extremely effective improvement over known methods.

In accordance with the method of the present invention for preparing α-APM by neutralizing an acid addition salt of α-APM with a base on an industrial scale, especially on a liter scale or larger, the fluidity of the liquid during neutralization is greatly improved, the solid-liquid separability of the α-APM crystals produced is improved, and the yield are noticeably improved. Additionally, the steps constituting the method are simplified. Therefore, the method of the present invention is very valuable for industrial use.

Other features of the invention will become apparent in the course of the following descriptions of exemplary embodiments which are given for illustration of the invention and are not intended to be limiting thereof.

EXAMPLES

A test for evaluating the filterability of α-APM crystals obtained in the examples was conducted by the method described below.

Method of Measuring Filtration Specific Cake Resistance

One liter of a sample to be tested was sampled and filtered through a top-feed suction filter system (leaf tester). The pressure difference during filtration was 70 mmHg, which was kept constant throughout the filtration. From the start of filtration, the amount of the filtrate $V(cm^3)$ was measured at regular intervals and plotted on a graph having the amount of the filtrate as the horizontal axis and the value $(\theta/V)$, obtained by dividing the time of filtration $\theta(sec)$ by the amount of the filtrate, as the vertical axis. The slope of the line $K(sec/ml^2)$ was obtained by the least squares method. The value $C'$, obtained by dividing the total amount (g) of the crystals in the slurry by the total amount $(cm^3)$ of the liquid in the slurry, is used in the following equation for specific cake resistance. The filtration area A was 93 $(cm^3)$; and the viscosity $\mu$ of the filtrate was 0.0135 (g/cm·sec). The specific cake resistance $\alpha$ thus calculated is a measure of the filterability of the sample. Samples having a lower value $\alpha$ are more easily filtered.

Equation of Specific Cake Resistance:

$$\alpha = 20 \cdot K \cdot A^2 \cdot PT / \mu \cdot C' \ (m/kg)$$

where $\alpha$ is the specific cake resistance (m/kg) of the filtered cake;

$\mu$ is the viscosity of the filtrate (g/cm·sec);

PT is the pressure difference $(dyne/cm^2)$ by the filtered cake and the filtration device $= \Delta P(mmHg) \times 1333.22$;

A is the filtration area $(cm^2)$; and $C'$ is the weight of the crystals per the unit volume of the liquid component in the slurry $(g/cm^3)$ = dry cake weight (g)/(wet cake weight (g) − dry cake weight (g) + amount of final filtrate $(cm^3)$).

EXAMPLE 1

110.8 g of wet crystals of α-APM hydrochloride (containing 62 wt.% of α-APM) were dissolved in 1400 ml of water at 28° C., which was adjusted to have a pH of 2.5 with 16 wt.% sodium carbonate solution to prepare an α-APM hydrochloride solution A. This was added dropwise to a suspension B of 25 g of α-APM suspended in 500 ml of water at 3.5° C., in a 2.5-liter jacketed separation flask through which cold water at 3.5° C. was circulated. Dropwise addition was continued at a constant addition rate while stirring with an anchor-shaped stirring blade having a blade diameter of 10 cm, at 200 rpm, over a period of 3 hours. During the addition, the temperature of the solution was adjusted to be from 3.5 to 5.0° C. and the pH of the same to be always 5.0 with 16 wt.% sodium carbonate solution. During the addition, rapid precipitation of crystals was not seen and the slurry maintained good fluidity. After the addition, the slurry obtained was subjected to the leaf test described above to obtain a good value of $9.8 \times 10^9$ (m/kg). The dry yield was 85.3 g (90.9%).

EXAMPLE 2

2358 g of wet crystals of α-APM hydrochloride were dissolved in 23 liters of water at 30° C. (6 g/dl as c-APM concentration), which was adjusted to have pH of 2.5 with 10 wt.% sodium carbonate to prepare an α-APM hydrochloride solution A. This was added dropwise to a jacketed flask (with stirring at 200 rpm) into which a coolant at 5° C. was circulated, at a constant rate of 15 ml/min. The flask contained the slurry as prepared by the method of Example 1 and adjusted to have pH of 4.8, as the receiving liquid B. During the dropwise addition, the flask was made to overflow so that the amount of liquid in the flask was always 5 liters. The pH of the liquid in the flask was adjusted to a constant 4.8 by dropwise addition of 10 wt.% sodium carbonate solution at a rate of 1.25 ml/min. The concentration of the solution was adjusted to maintain an α-APM concentration of 4.8 g/dl by adding an α-APM solution of 5° C. (α-APM concentration 0.6 g/dl) at a rate of from 2.7 to 3.1 ml/min. The continuous operation was effected for 24 hours, during which time rapid precipitation of crystals was not seen and the slurry maintained good fluidity. The overflowing slurry was received in a container cooled with ice and was continuously stirred. The overflowing slurry received in the container in the last one hour was subjected to the leaf test to obtain a result of $3.0 \times 10^{10}$ (m/kg).

COMPARATIVE EXAMPLE 1

240 g of wet crystals of α-APM hydrochloride (containing 62 wt.% of α-APM) were dissolved in 1900 ml of water at 28° C. in a 2.5-liter jacketed separable flask through which warm water at 30° C. was circulated, to prepare an α-APM hydrochloride solution. While the solution was maintained at a temperature of 28° C., 16 wt.% sodium carbonate solution was added dropwise at a constant rate (7 ml/min). The scheduled period before finish of neutralization was 30 minutes. Stirring was effected at 70 rpm with an anchor-shaped stirring blade having a blade diameter of 10 cm, but the liquid lost fluidity with precipitation of crystals (pH 3.0, after 16 minutes). The stirring stopped after 21 minutes after the start of the experiment. The contents of the flask had solidified.

COMPARATIVE EXAMPLE 2

150.3 g of wet crystals of α-APM hydrochloride (containing 62 wt.% α-APM) were dissolved in 1900 ml of water at 28° C. in a 2.5-liter jacketed separable flask through which warm water at 30° C. was circulated, to prepare an α-APM hydrochloride solution. While the solution was maintained at a temperature of 28° C., 16 wt.% sodium carbonate solution was added dropwise at a constant rate over a period of 6 hours until the pH value of the solution became 5 (21.7 ml/hr). Stirring was effected at 200 rpm with an anchor-shaped stirring blade having a blade diameter of 10 cm, but the surface portion of the liquid lost fluidity with precipitation of crystals (pH 3.4) so that smooth operation could no longer be conducted. The stirring rate was changed to 300 rpm in the course of the process. After completion of the addition, the system was cooled to 5° C. over a period of 3 hours, and the slurry obtained was subjected to the leaf test. The result was $1.0 \times 10^{11}$ (m/kg). The dry yield was 83.9 g (86%).

COMPARATIVE EXAMPLE 3

100.2 g of wet crystals of α-APM hydrochloride (containing 62 wt.% of α-APM) were dissolved in 1900 ml of water at 28° C. in a 2.5-liter jacketed separable flask through which warm water at 30° C. was circulated, to prepare an α-APM hydrochloride solution. While the solution was maintained at a temperature of 28° C., 16 wt.% sodium carbonate solution was added dropwise at a constant rate over a period of 4 hours and 40 minutes until the pH value of the solution became 5 (19.6 ml/hr). Stirring was effected at 200 rpm with an anchor-shaped stirring blade having a blade diameter of 8 cm. Even after precipitation of crystals, the contents in the flask maintained fluidity. After completion of the addition, the system was cooled to 5° C. over a period of 2 hours, and the slurry obtained was subjected to the leaf test. The result was $1.08 \times 10^{11}$ (m/kg). The dry yield was 52.37 g (84%).

Obviously, numerous modifications and variations of the present invention are possible in light of the above teachings. It is therefore to be understood that within the scope of the appended claims, the invention may be practiced otherwise than as specifically described herein.

What is claimed as new and desired to be secured by Letters Patent of the United States is:

1. A method of preparing α-L-aspartyl-L-phenylalanine methyl ester, comprising:
   neutralizing a solution or suspension A of an acid addition salt of α-L-aspartyl-L-phenylalanine methyl ester having a concentration of said acid addition salt of 3 wt.% or more, a pH of 3 or less and a temperature of 50° C. or lower, with a base by adding said solution or suspension A into an aqueous medium B with stirring to form a mixture, wherein said base is present in said aqueous medium B and/or is added simultaneously with solution or suspension A to said aqueous medium B, said mixture having a temperature of 40° C. or lower and a pH of 3 or more, thereby forming crystals of α-L-aspartyl-L-phenylalanine methyl ester.

2. The method of claim 1, further comprising adding a base to said solution or suspension A to maintain a solution or suspension pH of from 2-3 prior to said adding and stirring with said aqueous medium B.

3. The method of claim 1, comprising simultaneously adding a base to said aqueous medium B while adding and stirring said solution or suspension A into said aqueous medium B, thereby maintaining the pH of said mixture at pH 3-6.

4. The method of claim 1, wherein said mixture has a final pH of 4-6.

5. The method of claim 1, further comprising cooling said mixture to 30° C. or less during or after adding and mixing said solution or suspension A into said aqueous medium B.

6. The method of claim 1, wherein said mixing, neutralizing and/or cooling steps are carried out stepwise in a plurality of reaction containers.

7. The method of claim 1, wherein said acid addition salt is a hydrochloride salt.

* * * * *